United States Patent
Ichim et al.

(10) Patent No.: US 10,792,310 B2
(45) Date of Patent: Oct. 6, 2020

(54) METHODS FOR TREATMENT OF PREMATURE OVARIAN FAILURE AND OVARIAN AGING USING REGENERATIVE CELLS

(71) Applicant: Creative Medical Technologies, Inc., Phoenix, AZ (US)

(72) Inventors: Thomas Ichim, San Diego, CA (US); Amit Patel, Salt Lake City, UT (US)

(73) Assignee: Creative Medical Technologies, Inc., Phoenix, AZ (US)

( * ) Notice: Subject to any disclaimer, the term of this patent is extended or adjusted under 35 U.S.C. 154(b) by 640 days.

(21) Appl. No.: 15/652,213

(22) Filed: Jul. 17, 2017

(65) Prior Publication Data

US 2018/0015127 A1    Jan. 18, 2018

Related U.S. Application Data

(60) Provisional application No. 62/363,633, filed on Jul. 18, 2016.

(51) Int. Cl.

| | |
|---|---|
| *A61K 35/44* | (2015.01) |
| *A61K 35/28* | (2015.01) |
| *A61K 31/56* | (2006.01) |
| *A61K 35/22* | (2015.01) |
| *A61K 9/00* | (2006.01) |
| *C12N 5/0775* | (2010.01) |
| *A61K 31/57* | (2006.01) |
| *A61K 31/565* | (2006.01) |
| *A61K 45/06* | (2006.01) |
| *A61K 35/17* | (2015.01) |
| *C12N 5/071* | (2010.01) |
| *A61K 35/51* | (2015.01) |
| *A61K 35/12* | (2015.01) |

(52) U.S. Cl.
CPC ............ *A61K 35/44* (2013.01); *A61K 9/0019* (2013.01); *A61K 31/565* (2013.01); *A61K 31/57* (2013.01); *A61K 35/17* (2013.01); *A61K 35/22* (2013.01); *A61K 35/28* (2013.01); *A61K 35/51* (2013.01); *A61K 45/06* (2013.01); *C12N 5/0662* (2013.01); *C12N 5/0663* (2013.01); *C12N 5/0692* (2013.01); *A61K 2035/124* (2013.01); *C12N 2320/30* (2013.01); *C12N 2501/392* (2013.01)

(58) Field of Classification Search
CPC ...... A61K 35/44; A61K 35/22; A61K 9/0019; A61K 35/28; A61K 2035/124; C12N 5/0662; C12N 2320/30
See application file for complete search history.

(56) References Cited

PUBLICATIONS

Alev et al. "Endothelial Progenitor Cells: A Novel Tool for the Therapy of Ischemic Diseases." Antioxidants & Redox Signaling vol. 15, No. 4, 2011. (Year: 2011).*

Cha et al. "Effect of Human Endothelial Progenitor Cell (EPC)- or Mouse Vascular Endothelial Growth Factor-Derived Vessel Formation on the Survival of Vitrified/Warmed Mouse Ovarian Grafts." Reproductive Sciences 2014, vol. 21(7). (Year: 2014).*

Li et al. "Influence of Mesenchymal Stem Cells with Endothelial Progenitor Cells in Co-culture on Osteogenesis and Angiogenesis: An In Vitro Study." Archives of Medical Research 44 (2013) 504-513. (Year: 2013).*

* cited by examiner

*Primary Examiner* — Kevin K Hill
*Assistant Examiner* — James Joseph Graber
(74) *Attorney, Agent, or Firm* — Baumgartner Patent Law; Marc Baumgartner

(57) ABSTRACT

This invention pertains to the field of ovarian aging and premature ovarian failure. Specifically, we herein disclose methods for treating these conditions using endothelial progenitor cells alone or in combination with mesenchymal stem cells. Furthermore, these cell-based therapies can be utilized in combination with estrogen and progesterone receptor ligands to enhance the therapeutic activity of said cells for restoring or maintaining ovarian function and female fertility.

4 Claims, No Drawings

METHODS FOR TREATMENT OF PREMATURE OVARIAN FAILURE AND OVARIAN AGING USING REGENERATIVE CELLS

CROSS-REFERENCE TO RELATED APPLICATIONS

This application claims priority to U.S. Provisional Application No. 62/363,633, filed Jul. 18, 2016, which is incorporated herein by reference in its entirety.

FIELD OF THE INVENTION

The invention pertains to the field of ovarian aging and premature ovarian failure. Specifically, this invention relates to regenerative cell-based therapies for treating women afflicted with premature ovarian failure or at-risk for developing said condition. In a preferred embodiment of the present invention, methods are disclosed for administering endothelial progenitor cells to an individual with premature ovarian failure. In certain aspects of the invention, said endothelial progenitor cells can be administered along or in combination with estradiol and/or progesterone. Said mesenchymal stem cells can also be treated ex vivo with estradiol and/or progesterone, and administered to patients in need thereof. Said mesenchymal stem cells can be co-administered with estradiol and/or progesterone in vivo to treat said patient. In other embodiments of the present invention, methods are disclosed for using endothelial progenitor cells in combination with mesenchymal stem cells. Said endothelial progenitor cells and/or said mesenchymal stem cells may be pre-treated with estradiol and/or progesterone or said hormones can be co-administered along with said cell population(s) to an individual in need thereof.

BACKGROUND OF THE INVENTION

Ovaries contain follicles at various stages of development and corpora lutea, either active or at various stages of involution. The primordial follicles represent a reserve of germ cells for the entire reproductive life of the female. Ovarian aging resulting in ovarian failure and menopause is an on-going process. Of the early signs of ovarian aging, failure to adequately respond to ovarian stimulation, irregular menstrual cycles, and loss of follicle function occurs. It is believed that the process of physiological reproductive aging stems from the decrease in the number and quality of the oocytes in the ovarian cortex follicles. This reduction of the oocytes accelerates with aging and increases after age 38. The first sign of reproductive aging is marked by a reduction in the length of the menstrual cycle, beginning on average by age 30 [1]. Subsequently, ovarian aging begins at approximately age 46 with full blown menopause occurring on average by age 51 (the range is approximately between ages 40-60). Despite increases in life expectancy, menopausal age has not changed in the last century [1]. Since there has been a societal trend toward delaying childbirth until later in life, a great desire has arisen to address ovarian aging, preserve fertility and extend the child-bearing years.

Premature ovarian failure (POF), also referred to as premature ovarian insufficiency (POI) or premature menopause, is characterized by a loss of ovarian function marked by cessation of ovarian function and premature ovarian follicle depletion before 40 years of age. POF can occur due to limited numbers of ovarian follicles or maturation defects of the follicles, leading to infertility [2]. This condition is distinct from naturally-occurring menopause insofar as POF can be reversible (normal pregnancy can occur in 5-10% of these patients ([3]) [4]. Management of this condition involves hormone replacement therapy to address the side effects and infertility treatments. The ovaries produce little to no estrogen in ovarian failure, resulting in loss of the negative feedback system to the hypothalamus and pituitary glands. In turn, the dysregulated hormonal signals precipitate many of the side effects associated with the condition, including hot flashes, night sweats, mood changes, and impaired concentration.

The etiology of POF is believed to be multi-factorial and, in most clinical cases, the underlying cause is not identified. Genetic pathogenesis, namely, X-chromosome-linked defects, are thought to account for some cases of POF [5]. It has also been suggested that some cases of POF of unknown etiology may represent a variation of the normal course of menopause whereby ovarian aging has occurred earlier than the norm. Mutations in genes that exert hormonal influences on follicle function or genes that affect the rate of initial selection from the primordial follicle pool may account for decreases in reproductive life span. These genes may include genes encoding growth differentiation (GD) factors, bone morphogenetic proteins, and angiogenesis-promoting factors such as vascular endothelial growth factor (VEGF), its receptors, hepatocyte growth factor (HGF), placental growth factor (PGF), and transforming growth factor-beta (TGF-beta). Immunological changes have also been implicated in POI including autoimmune-mediated destruction of granulosa cells (GCs), oocytes, and the zona pellucida [6-8]. Various autoantibodies associated with POF have shown poor sensitivity or specificity, such that estimates of POF range anywhere from 7%, and 50 to 70% of women with POF. POF is associated with Addison's disease, marked by the presence of antibodies to steroid cells [9]. Steroidal-cell antibodies were detected in ovarian biopsies performed in s a small cohort of women with spontaneous POI, 100% of women with SCAs were found to have $CD3^+$ lymphocytic infiltrates on ovarian biopsy, indicative of T-cell-mediated oophoritis [10]. Despite this, there is evidence that antibodies themselves may not be primarily responsible for precipitating disease and/or that yet-undetermined antigens are actually responsible for precipitating disease. Since the pathogenesis of POF remains incompletely defined, the efficacy of immunologically-directed treatment is unpredictable.

Chemotherapeutic agents, including alkylating agents, antimetabolites, aneuploidy inducers, radiomimetics and topoisomerase II inhibitors, can have variable impacts in precipitating POF. Mechanistically, these agents may cause ovarian cell apoptosis, impair local hormone regulation needed for follicular function, or they may prevent normal interactions between oocytes and granulosa cells, which provide physical support and microenvironment required for the developing oocyte. Chemotherapy-induced ovarian failure may be reversible; however, in other cases, the damage is progressive and dysfunction is permanent. Such ovarian failure is diagnosed by irreversible amenorrhoea lasting for several months (>12 months) following chemotherapy and a follicle stimulating hormone level of > or =30 MIU/mL (Molina JR 2005).

Women diagnosed with POF often seek hormone replacement therapies to manage their symptoms as well as to manage possible long-term health consequences that are similar to those associated with menopause except that they start earlier in POF. The use of bioidentical hormones, including progesterone, estradiol, and estriol, in hormone replacement therapy has sparked intense debate. One concern has been their relative safety compared with commonly-used synthetic and animal-derive hormone sources which include as conjugated equine estrogens (CEE), medroxyprogesterone acetate (MPA), and other synthetic progestins. Proponents for bioidentical hormones claim that they are safer than comparable synthetic and nonhuman versions. However, the US Food and Drug Administration has not approved many of these regimens and there is little or no concrete evidence to support claims pertaining to safety or efficacy of bioidentical hormones. While hormone replacement therapy has been implicated in an increased risk of vascular disease, osteoporosis and even ovarian cancer and breast cancer for these patients, the safety of HRT is a contentious issue [11].

The estrogen receptor (ER) is a member of the nuclear hormone receptor superfamily, which mediates the activity of estrogens in the regulation of a number of important physiological processes, including the development and function of the female reproductive system and the maintenance of bone density and cardiovascular health. Estrogen has multifunctional roles influencing growth, differentiation and metabolism in many tissues. Estrogen exerts its functions via its receptors that exist in multiple progenitor cells of bone marrow and adipose tissue. The primary ER ligands are estriol (also referred to herein as E3), estradiol, and estrone, particularly 17-β estradiol; however, foreign ligands, including artificial ligands, can be introduced into cells to serve as ER agonists.

At a molecular level, changes in angiogenic and endothelial cell-related markers also correlate with both POF and ovarian aging. Indeed, vascular endothelial dysfunction originating from sex steroid deficiency has been identified as a feature of POF, and, accordingly, estrogen and progesterone replacement therapies can restore endothelial function [12]. However, in considering the cause and effect relationship between vascular function and ovarian function, it is not clear whether vascular health of women correlates with their reproductive age and there is conflicting information whether restoring proper angiogenesis could improve fertility or delay infertility.

The initiation and maintenance of growth of the ovarian follicles relies on the presence of an extensive microvasculture. Experiments in which inhibitors of angiogenesis were administered to mammals (for example, soluble VEGF receptor 1 inhibitors) showed impaired of ovulation and attenuated luteal function. The importance of the degree of perfusion of the follicle microenvironment is also exemplified by findings that fertilization and developmental potential is higher for oocytes with high levels of vascularization and high levels of oxygenation (>3%) [13, 14]. One study showed that embryos originating from oocytes developed in well-vascularized follicles have higher implantation rates than those originating from oocytes developed in follicles with poor vascularization [15]. Moreover, cross-talk between oocytes and GC involves signaling pathways involved in cell proliferation, differentiation, and survival/apoptosis (for example, the Notch pathway) working in concert with pathways for angiogenesis (notably, VEGF and its receptors that are expressed on both oocytes and GCs). These proteins may have angiogenic roles by acting on endothelium that feeds the ovarian follicle vasculature and/or they may have non-classical (non-angiogenic) roles in this milieu (for example, when expressed by or acting on GCs) [16]. For example, Greenaway et al. [16] demonstrated that VEGF treatment of serum-starved and cytokine-exposed granulosa cells resulted in enhanced survival, an effect that was ameliorated by blockade of Flk-1/KDR signaling. Reduced expression of Flk-1/KDR was also associated with follicle atresia, suggesting involvement of this pathway in health of the follicles. Along with these possible targets of therapy to improve female fertility, other proteins that may regulate angiogenesis in the follicle either directly or indirectly could also be modulated therapeutically to rescue ovarian function including but not limited to angiogenesis including angiopoietins, natriuretic peptides, connective tissue growth factors (CTGF), thrombospondins, cell adhesion proteins (for example, VE-cadherin, claudin-5), and other components of the extracellular matrix.

The ovary is a rare anatomic location where neovascularization occurs. Angiogenesis in the ovaries is controlled by VEGF, for which mRNA is mainly expressed in granulosa cells of the cumulus oophorus and thecal cells of large antral follicles but also in epithelial cells that are progenitors of ovarian cancer cells [17]. Notably, VEGF and other angiogenic factors are considered critical driving forces in ovarian cancer [18]. Moreover, the rising levels of gonadotropins (luteinizing hormone (LH) and follicle stimulating hormone (FSH)) that are present during menopause and in POF can contribute significant to increased angiogenesis, marked by proliferation of endothelial cells, that fuels ovarian cancer, as has been demonstrated in numerous experimental systems [18]. Given that angiogenesis is required for ovarian function but can also promote tumorigenesis, the pathways of angiogenesis must be carefully regulated when therapies for treating POF and ovarian aging are being considered, including in cellular therapies where stem cells and progenitor cell populations are contemplated as therapeutic agents for these disorders.

DETAILED DESCRIPTION OF THE INVENTION

The present invention describes methods for using endothelial progenitor cells (EPC) and/or mesenchymal stem cells (MSC) for treatment or prevention of ovarian aging, premature ovarian failure, and, in general, infertility in females where ovarian function is substantially inhibited. The present invention also discloses methods for using hormones, estradiol and/or progenitor in order to modulate the activity of said EPC and MSC for the treatment or prevention of ovarian aging, premature ovarian failure, and female infertility in general. Said endothelial progenitor cells and/or MSC can be co-administered with estradiol and/or progesterone to a patient in need thereof. Alternatively, said EPC and/or MSC may be pre-treated with estradiol and/or progesterone and then administered to a patient in need thereof. The latter embodiment capitalizes on the responsiveness of EPC and MSC to estradiol and progesterone through their expression of receptors for these hormones.

As used herein, the term "regenerative cell" refers to EPC and/or MSC.

As used herein, the term "ovarian aging" may refer to a reduction in follicle numbers and/or reduced quality or quantity of oocytes, or other sequelae related to ovarian health that are associated with a loss of natural fertility in women.

As used herein, the term "therapeutic activity" refers to any activity of cells and/or other agents that reverses or improves ovarian aging or POF; specifically, cellular and/or molecular effects within the female reproductive tract and, more specifically, within the ovaries or ovarian follicles. For example, said therapeutic activity may comprise an increase in angiogenesis, neoangiogenesis, or vascular function in the ovary that has beneficial effects against the pathological changes in the ovary observed in an individual diagnosed with POF or ovarian aging.

As used herein, the term "endothelial progenitor cell" or "EPC" refers to a mononuclear cell having the developmental potential to form endothelial cells and expressing markers from a group that includes CD34, CD133, CD144, CD146 and Flk1. EPC may refer to any tissue resident or circulating blood cell that can be induced to display endothelial characteristics including EPC isolated from bone marrow, monocytic EPC (derived from peripheral blood mononuclear cells), and hemangioblastic EPC.

In the context of the present invention, said EPC can be isolated directly from tissue sources and/or these cells may be cultured in vitro. For example, peripheral blood mononuclear cells (PBMC) can be isolated by density gradient centrifugation at 1600 rpm for 60 min with Ficoll-Paque separating solution, the cellular PBMC fraction isolated and counted, and then subjected to fluorescence-activated cell sorting (FACS) analysis. The circulating EPC can be identified on the basis of expression of VEGF-R2, AC133 and CD34. Culture of EPC can also be performed to induce their proliferation and thereby increase their numbers for therapeutic use. Proliferation of EPC may be achieved by culturing the PBMCs or enriched EPC in the presence of one or more growth factors including VEGF, fibroblast growth factor-2 (FGF-2), epidermal growth factor (EGF) and/or insulin-like growth factor-1 (IGF-1).

As used herein, the term "mesenchymal stem cell" refers to a multipotent stem cell that can differentiate into a variety of cell types, including: osteoblasts (bone cells), chondrocytes (cartilage cells), and adipocytes (fat cells).

The mesenchymal stem cell population preferably expresses one or more markers selected from the group consisting of: STRO-1, CD105, CD54, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1. According to more specific embodiments, the mesenchymal stem cell population does not express substantial levels of the markers selected from the group consisting of: HLA-DR, CD117, and CD45.

The MSC population can be derived from sources selected from the group consisting of: bone marrow, adipose tissue, umbilical cord blood, placental tissue, peripheral blood mononuclear cells, endometrial tissue, differentiated embryonic stem cells, and differentiated progenitor cells.

MSC may be autologous or allogeneic or, if allogeneic, derived from male or female donors.

In one embodiment of the present invention, mesenchymal cells are generated through culture. U.S. Pat. No. 5,942,225 (incorporated by reference herein in its entirety) teaches culture techniques and additives for differentiation of such stem cells which can be used in the context of the present invention to produce increased numbers of cells with angiogenic capability. U.S. Pat. No. 6,387,369 (incorporated by reference herein in its entirety) teaches use of mesenchymal stem cells for regeneration of cardiac tissue, in accordance with published literature [87, 88] stem cells generated through these means have angiogeneic activity and therefore may be utilized in the context of the current invention. In the context of the present invention, mesenchymal stem cells may evoke angiogenesis through production of factors such as vascular endothelial growth factor, hepatocyte growth factor, adrenomedullin, and insulin-like growth factor-1 [89].

MSC are classically obtained from bone marrow for clinical use. Alternative sources of mesenchymal stem cells include adipose tissue, placental tissue and cord blood. In the context of the present invention, MSC may be allogeneic or autologous. In one embodiment of the present invention, MSC are transfected with genes to increase their angiogenic and/or to modify their immunogenicity or their immunomodulatory potential. Transfection may be performed with genes encoding VEGF, FGF1, FGF2, FGF4, angiopoietin, HLA-G, IL-10, IL-13, IL-13, IL-4, TGF-beta, IL-17, PD-1L, FasL, TNF-receptor, or IL-1 receptor antagonist. The ability of said MSC to induce angiogenesis may be assessed in vitro prior to administration of said MSC, either transfected with additional genes or non-transfected, to an individual in need thereof. The ability of MSC to induce angiogenesis can be determined by measuring the induction of proliferation of human umbilical vein derived endothelial cells using methods that are known in the art.

One specific embodiment of this invention includes methods of treating POF or addressing ovarian aging in a mammal through the steps of: a) Identifying a mammal with POF or ovarian aging; b) Administering EPC to said mammal; c) Measuring ovarian function following administration of said cell population.

Another embodiment of the present invention involves methods of treating POF or addressing ovarian aging in a mammal through the steps of: a) Identifying a mammal with POF or ovarian aging; and, b) Administering EPC to said mammal; c) Administering MSC to said mammal; and, d) Measuring ovarian function following administration following administration of said cell populations.

In one embodiment, EPC are provided in absence of MSC with the purpose that EPC will induce angiogenesis and/or increase perfusion in the ovaries. In some embodiments, the therapy is performed in combination with a growth factor or a plurality of growth factors. Said growth factors may be used to treat EPC in vitro prior to administration of said EPC to an individual in need thereof. Other growth factors may be co-administered with EPC to an individual in need thereof in order to increase angiogenesis and/or perfusion for enhancing ovarian function. Said growth factors may include, without limitation, angiogenic factors and other molecules competent to induce angiogenesis, including acidic and basic fibroblast growth factors, vascular endothelial growth factor, hif-1, epidermal growth factor, transforming growth factor .alpha. and .beta., platelet-derived endothelial growth factor, platelet-derived growth factor, hepatocyte growth factor and insulin like growth factor; growth factors; BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16.

In other embodiments, MSC are provided with EPC to an individual in need thereof. Said MSC and EPC may be administered concomitantly, separately, by the same or different routes of administration, and at the same time or different times to said individual in need thereof. In the context of the present invention, MSC may be provided as immunomodulatory cells to enhance the engraftment, survival or angiogenic potential of EPC. Without being bound by theory, said MSC may be pre-treated or co-administered with growth factors or cytokines as described herein for EPC.

In preferred embodiments of this invention, EPC are provided together with MSC as therapeutic cells for inducing angiogenesis and/or increasing perfusion in the ovaries as a treatment for POF and/or ovarian aging, in order to augment ovarian function and to improve female fertility.

In a preferred embodiment of the present invention, EPC and/or MSC are injected into the ovaries and/or ligaments through laparoscopy using techniques established in the art. EPC and/or MSC may also be administered to an individual in need thereof via one or more of the following routes of administration: intravenously, intramuscularly, transdermally, intrathecally, intravaginally, or intrauterinally.

Within the scope of this invention, ovarian function and parameters of female fertility may be monitored following administration of EPC and/or MSC to an individual in need thereof. Accordingly, one or more of several methods may be implemented. Ultrasonographic assessment of ovarian aging include antral follicle count, ovarian volume, and ovarian blood flow measurement may be performed. Transvaginal color Doppler ultrasonography may be performed to evaluate blood flow. Blood testing for follicle-stimulating hormone (FSH), luteinizing hormone (LH), estradiol, inhibin B, and FSH/LH ratio can be performed. Anti-Müllerian hormone (AMH) can be measured to evaluate ovarian aging. AMH is a dimeric glycoprotein secreted to the serum from the granulosa cells of early developing follicles, especially from pre-antral and small antral follicles, and thus is correlated with antral follicle count. The dynamic tests that can be performed include clomiphene citrate challenge test (CCCT) and Gonadotropin Releasing Hormone (GnRH) agonist stimulation. Ovary- or adrenal-specific antibody testing may be performed. Fertility testing may also be performed. For example, basal body temperature may be measured or ovulation predictor kits known in the art may be utilized to evaluate, where applicable, if ovulation has occurred.

In yet other embodiments of the present invention, EPC, MSC, or both populations are cultured in the presence of 17-beta estradiol prior to administration to an individual in need thereof. The concentration of 17-beta estradiol required in culture for generating therapeutic cell population(s) will be gauged by evaluation of the functional characteristics of said cultured cells conducted in preliminary tests prior to administration to an individual in need thereof. For example, one or more of the following assays will be performed:

1. Proliferation of MSC. For example, using techniques known in the art, MSC will be placed into each well of 96-well plates and cultured in medium supplemented with 17-beta estradiol or without. The 17-beta estradiol concentrations may range from $10^{-6}$ to $10^{-12}$ M. The cell proliferation was measured using an MTS-based colorimetric methods.

2. MSC surface marker expression: MSC may be evaluated by flow cytometry using antihuman antibodies positive to CD105, CD166, CD29, and CD44 and negative to CD14, CD34, and CD45, and other surface markers not mentioned herein. MSC can be compared following culture with 17-beta estradiol or without.

3. Differentiation capacity: Using methods known in the art, the ability of MSC from 17-beta estradiol vs. control cultures to exhibit adipogenic, osteogenic, chondrocytic, and/or endothelial lineage cells can be evaluated and compared cytokine and growth factor production in MSC cultured with 17-beta estradiol vs. untreated MSC including, but not limited to, the measurement of VEGF, HGF, IGF-1, and other factors using techniques such as enzyme-linked immunosorbent assay (ELISA).

In the context of the present invention, "angiogenic potential" of a cell refers to its expression of angiogenesis-related genes and/or the ability of the cell to promote angiogenesis, either directly or indirectly as measured in laboratory tests or in vivo. Said angiogenesis-related genes may be selected from the list consisting of: MDK, PDGFB, endoglin, neuropilin 1, Rho GTPase activing protein 22, GATA binding protein 2, heparin sulfate 6-O-sulfotransferase 1, FMS-like tyrosine kinase, Notch gene homolog 1, heparin-binding EGF-like growth factor, chemokine (C-X3-C motif) ligand 1, fibroblast growth factor receptor 2, platelet derived growth factor subunit A, transforming growth factor beta 2, Kruppel-like factor 5, endothelin 1, tumor necrosis factor receptor superfamily members, follistatin, vascular endothelial growth factor, and any receptors for the above-mentioned angiogenesis-related genes.

Said "angiogenic potential" of EPC or MSC can be monitored using techniques known in the art. For example, in one embodiment, cells can be plated on collagen-coated plates, and cultured to determine whether colonies with a distinctive cobblestone morphology emerge, indicative of endothelial-like cells.

In another embodiment of the present invention, EPC and MSC are contacted with a culture medium supplemented with an effective amount of one or more estrogen receptor ligands selected from the group consisting of estriol, estradiol, estrone, and combinations thereof, more preferably including 17-beta estradiol, estriol (E3) or both. In one embodiment, these estrogen receptor ligands are used to enhance angiogenic potential of EPC and/or MSC. In other embodiments of the present invention, these estrogen receptor ligands are utilized to augment proliferation and/or survival of EPC and/or MSC. The amount (or concentration) of estrogen receptor ligands cultured with EPC and/or MSC for inducing proliferation or survival may be the same or different than the amount (concentration) required for augmenting angiogenic potential. In a further embodiment of the present invention, the concentration of estrogen receptor ligands is adjusted to modify the proliferation, survival or angiogenic potential of EPC and/or MSC.

In yet another embodiment, EPC, MSC or both populations are cultured in the presence of 17-beta estradiol plus progesterone prior to administration to an individual in need thereof.

In a preferred embodiment of the present invention, EPC and/or MSC are injected into the ovaries and/or ligaments using laparoscopy. EPC and/or MSC may also be administered to an individual in need thereof via one or more of the following routes of administration: intravenously, intramuscularly, transdermally, intrathecally, intravaginally, or intrauterinally.

One specific embodiment of this invention includes methods of treating POF or addressing ovarian aging in a mammal through the steps of: a) Identifying a mammal with POF or ovarian aging; b) Administering EPC to said mammal; c) Administering estradiol and progesterone to said mammal; and, d) Measuring ovarian function following administration of said cell population.

Another embodiment of the present invention involves methods of treating POF or addressing ovarian aging in a mammal through the steps of: a) Identifying a mammal with POF or ovarian aging; and, b) Administering EPC to said mammal; c) Administering MSC to said mammal; and, c) Administering estradiol and progesterone to said mammal; and, d) Measuring ovarian function following administration following administration of said cell populations.

In a preferred embodiment of the present invention, EPC and/or MSC are injected into the ovaries through laparoscopy using techniques established in the art. EPC and/or MSC may also be administered to an individual in need thereof via one or more of the following routes of administration: intravenously, intramuscularly, transdermally, intrathecally, intravaginally, or into the uterus.

A preferred embodiment of the present invention involves administration of estradiol and/or progesterone topically in a cream to an individual in need thereof. Preferably, said cream containing an estrogen receptor ligand and/or progesterone is administered to the skin of the inner thigh or, in general, in the pelvic region, of said individual. Examples of other modalities for delivery of estrogen and progesterone may include other topical preparations (eg. gels), ingested articles (tablet, lozenge, capsule, troches), and articles for transdermal absorption of hormone preparations (transdermal patch, impregnated matrices). The type and amount of hormones involved in the various bioidentical human hormone compositions, and the modalities used varies depending independently, or in conjunction with, the physiologic sequence based on the normal menstrual cycle pattern, and specific clinical syndromes involved. A single bioidentical hormone, or a combination of bioidentical hormones may be used with any particular modality.

In the context of the present invention, hormone therapies are administered along with cellular population(s) in order to enhance the therapeutic activity of said cellular therapies. Said hormone therapies comprising estrogen and progesterone receptor ligands are known in the art and are commonly utilized for the purpose of hormone replacement therapy.

In other embodiments of the present invention, the concentrations and/or quantities of circulating EPC are measured in an individual diagnosed with POF or ovarian aging and are used to guide the course of therapy with EPC and/or MSC and/or hormones. EPC as measured in the blood can have diagnostic and prognostic value in numerous indications. Accordingly, methods known in the art can be utilized to monitor circulating EPC in individuals with POF at time intervals before and following therapy; for example, using flow cytometry-based evaluation of venous blood. For example, this embodiment may be practiced by comparing circulating EPC concentrations in the blood before and after therapy and determining the statistical significance of these changes. This information can be utilized in order to determine whether said method of therapy should be repeated or whether said method of therapy has been effective in a given individual.

This invention can be practiced to improve the longevity of the female's reproductive lifespan, to preserve ovarian reserve, to preserve the functions of the follicles and GCs, as assessed over a period of months or years. One example may be the use of this invention for preserving fertility and ovarian function in an individual undergoing chemotherapy. Accordingly, the frequency of administration of said EPC and/or MSC as well as the frequency of administration of estradiol or other estrogen receptor ligands and/or progesterone can be adjusted. In one embodiment of the present invention, said therapeutic cell and/or hormone administration is performed to prolong the duration of each menstrual cycle, to prolong the time (in months or years) to menopause, to preserve ovarian reserve, and/or to improve follicular functions and restore or maintain fertility. As a corollary of the aforementioned therapeutic effects, hormone production may be restored to levels that are consistent with retained fertility and ovarian function as measured by blood testing.

REFERENCES

[1] Sukur, Y. E., I. B. Kivancli, and B. Ozmen, Ovarian aging and premature ovarian failure. J Turk Ger Gynecol Assoc, 2014. 15(3): p. 190-6.

[2] Shelling, A. N., Premature ovarian failure. Reproduction, 2010. 140(5): p. 633-41.

[3] van Kasteren, Y. M. and J. Schoemaker, Premature ovarian failure: a systematic review on therapeutic interventions to restore ovarian function and achieve pregnancy. Hum Reprod Update, 1999. 5(5): p. 483-92.

[4] Kalantaridou, S. N., S. R. Davis, and L. M. Nelson, Premature ovarian failure. Endocrinol Metab Clin North Am, 1998. 27(4): p. 989-1006.

[5] Davis, C. J., et al., Female sex preponderance for idiopathic familial premature ovarian failure suggests an X chromosome defect: opinion. Hum Reprod, 2000. 15(11): p. 2418-22.

[6] Rhim, S. H., et al., Autoimmune disease of the ovary induced by a ZP3 peptide from the mouse zona pellucida. J Clin Invest, 1992. 89(1): p. 28-35.

[7] Shivers, C. A. and B. S. Dunbar, Autoantibodies to zona pellucida: a possible cause for infertility in women. Science, 1977. 197(4308): p. 1082-4.

[8] van Weissenbruch, M. M., et al., Evidence for existence of immunoglobulins that block ovarian granulosa cell growth in vitro. A putative role in resistant ovary syndrome? J Clin Endocrinol Metab, 1991. 73(2): p. 360-7.

[9] Irvine, W. J., et al., Immunological aspects of premature ovarian failure associated with idiopathic Addison's disease. Lancet, 1968. 2(7574): p. 883-7.

[10] Bakalov, V. K., et al., Autoimmune oophoritis as a mechanism of follicular dysfunction in women with 46, XX spontaneous premature ovarian failure. Fertil Steril, 2005. 84(4): p. 958-65.

[11] Oparil, S., Hormone therapy of premature ovarian failure: the case for "natural" estrogen. Hypertension, 2009. 53(5): p. 745-6.

[12] Kalantaridou, S. N., et al., Premature ovarian failure, endothelial dysfunction and estrogen-progestogen replacement. Trends Endocrinol Metab, 2006. 17(3): p. 101-9.

[13] Redmer, D. A. and L. P. Reynolds, Angiogenesis in the ovary. Rev Reprod, 1996. 1(3): p. 182-92.

[14] Huey, S., et al., Perifollicular blood flow Doppler indices, but not follicular pO2, pCO2, or pH, predict oocyte developmental competence in in vitro fertilization. Fertil Steril, 1999. 72(4): p. 707-12.

[15] Borini, A., et al., Perifollicular vascularity and its relationship with oocyte maturity and IVF outcome. Ann N Y Acad Sci, 2001. 943: p. 64-7.

[16] Greenaway, J., et al., Vascular endothelial growth factor and its receptor, Flk-1/KDR, are cytoprotective in the extravascular compartment of the ovarian follicle. Endocrinology, 2004. 145(6): p. 2896-905.

[17] Dissen, G. A., et al., Immature rat ovaries become revascularized rapidly after autotransplantation and show a gonadotropin-dependent increase in angiogenic factor gene expression. Endocrinology, 1994. 134(3): p. 1146-54.

[18] Schiffenbauer, Y. S., et al., Loss of ovarian function promotes angiogenesis in human ovarian carcinoma. Proc Natl Acad Sci USA, 1997. 94(24): p. 13203-8.

The invention claimed is:

1. A method for addressing ovarian aging or premature ovarian failure in an individual through the steps of:
 a) diagnosing an individual with premature ovarian failure or ovarian aging;
 b) administering endothelial progenitor cells to said individual; and
 c) measuring ovarian function following administration of endothelial progenitor cells to said individual.

2. A method for addressing ovarian aging or premature ovarian failure in an individual through the steps of:
   a) diagnosing an individual with premature ovarian failure or ovarian aging;
   b) administering endothelial progenitor cells to said individual;
   c) administering mesenchymal stem cells to said individual; and,
   d) measuring ovarian function following administration of said cell populations to said individual.

3. A method for addressing ovarian aging or premature ovarian failure in a mammal through the steps of:
   a) identifying a mammal with premature ovarian failure or ovarian aging;
   b) administering endothelial progenitor cells to said mammal;
   c) administering estradiol and progesterone to said mammal; and
   d) measuring ovarian function following administration of said cell population and hormones.

4. A method for addressing ovarian aging or premature ovarian failure in an individual through the steps of:
   a) diagnosing an individual with premature ovarian failure or ovarian aging;
   b) administering endothelial progenitor cells to said individual;
   c) administering mesenchymal stem cells to said individual;
   d) administering estradiol and progesterone to said individual; and
   e) measuring ovarian function following administration of said cell populations and hormones.

* * * * *